(12) United States Patent
Zhang (10) Patent No.: US 7,876,251 B2
(45) Date of Patent: Jan. 25, 2011

(54) SYSTEM FOR PROCESSING PATIENT MONITORING SIGNALS

(75) Inventor: Hongxuan Zhang, Palatine, IL (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 0 days.

(21) Appl. No.: 12/574,586

(22) Filed: Oct. 6, 2009

(65) Prior Publication Data

US 2010/0097259 A1    Apr. 22, 2010

Related U.S. Application Data

(60) Provisional application No. 61/107,380, filed on Oct. 22, 2008.

(51) Int. Cl.
*H03M 1/12* (2006.01)
(52) U.S. Cl. .................. 341/155; 341/123; 341/159
(58) Field of Classification Search ............ 341/118, 341/155, 167, 120, 126; 600/301, 509
See application file for complete search history.

(56) References Cited

U.S. PATENT DOCUMENTS

| | | | |
|---|---|---|---|
| 4,594,576 A | 6/1986 | Fujii | |
| 5,187,482 A | 2/1993 | Tiemann et al. | |
| 5,241,310 A | 8/1993 | Tiemann | |
| 5,382,956 A * | 1/1995 | Baumgartner et al. | ....... 341/155 |
| 5,477,472 A | 12/1995 | Wise et al. | |
| 5,691,720 A | 11/1997 | Wang et al. | |
| 5,817,133 A | 10/1998 | Houben | |
| 5,963,160 A | 10/1999 | Wilson et al. | |
| 6,191,718 B1 | 2/2001 | Matsumoto | |
| 6,240,132 B1 | 5/2001 | Yedid | |
| 6,462,693 B1 | 10/2002 | Rivoir | |
| 6,584,162 B1 | 6/2003 | Tinker | |
| 6,642,863 B1 | 11/2003 | Venkitachalam et al. | |
| 6,717,540 B1 | 4/2004 | Kamas et al. | |
| 6,760,623 B2 * | 7/2004 | Stahmann et al. | ............ 607/9 |
| 6,943,716 B2 | 9/2005 | Mallinson | |
| 6,999,014 B2 | 2/2006 | Le Men et al. | |
| 7,148,834 B2 | 12/2006 | da Fonte Dias et al. | |
| 7,248,200 B2 | 7/2007 | Komuro et al. | |
| 7,292,168 B2 * | 11/2007 | Wesselink et al. | .......... 341/123 |
| 7,295,645 B1 | 11/2007 | El-Ghoroury et al. | |
| 7,330,138 B2 | 2/2008 | Mallinson et al. | |

(Continued)

*Primary Examiner*—Linh V Nguyen
(74) *Attorney, Agent, or Firm*—Alexander J Burke (57) ABSTRACT

A patient monitoring signal processing system adaptively varies medical signal data rate. The system uses an analog to digital converter for digitizing an analog cyclically varying input signal derived from a patient in response to a sampling clock input. The sampling clock determines frequency of analog to digital sampling of the analog input signal by the analog to digital converter. A detector detects first and second different signal portions within a cycle of the cyclically varying input signal. A control processor coupled to the analog to digital converter and the detector, provides the sampling clock and adaptively determines first and second different frequencies of the sampling clock to be used in sampling within detected corresponding first and second different signal portions of the cyclically varying input signal in response to predetermined information indicating a frequency of a signal component of the cyclically varying input signal in the first signal portion is higher than a frequency of a signal component of the cyclically varying input signal in the second signal portion. Also the first frequency is higher than the second frequency of the first and second different frequencies.

19 Claims, 5 Drawing Sheets

U.S. PATENT DOCUMENTS

| | | |
|---|---|---|
| 7,336,208 B2 | 2/2008 | Van Den Enden et al. |
| 7,382,304 B2 * | 6/2008 | Stein .......................... 341/155 |
| 7,429,939 B2 * | 9/2008 | Xu ............................. 341/120 |
| 7,474,247 B1 * | 1/2009 | Heinks et al. ............... 341/155 |
| 7,623,053 B2 * | 11/2009 | Terry et al. ................. 341/143 |
| 7,668,588 B2 * | 2/2010 | Kovacs ....................... 600/509 |
| 2003/0067404 A1 | 4/2003 | Ruha |
| 2003/0078007 A1 | 4/2003 | Parssinen et al. |
| 2005/0286619 A1 | 12/2005 | Haddadin et al. |
| 2009/0028365 A1 * | 1/2009 | Nygard et al. ............... 381/312 |

\* cited by examiner

SYSTEM FOR PROCESSING PATIENT MONITORING SIGNALS

This is a non-provisional application of provisional application Ser. No. 61/107,380 filed Oct. 22, 2008, by H. Zhang.

FIELD OF INVENTION

This invention concerns a patient monitoring signal processing system for adaptively varying medical signal data rate, in response to an adaptively varied sampling clock.

BACKGROUND OF INVENTION

Medical signals are typically acquired using linear and uniform sampling and data acquisition. Known data conversion systems usually require sampling at two times the maximum frequency of the medical signals (according to the Nyquist—Shannon sampling theorem) to achieve accurate signal sampling. This may result in over-sampling and redundant data acquisition for low frequency portions of a signal, for example, such as rest portions of a heart activity signal (e.g., an ECG signal). Additionally, the over sampling and data conversion of medical signals may result in unwanted effects and inefficient use of a medical device and system as well as burdening of interface electronic through resource intensive data compression and transmission and additional signal delay. Known medical signal sampling systems uniformly process different portions of medical signals and utilize high sampling rate for different parts of a medical signal, irrespective of frequency and information content. A system according to invention principles addresses these deficiencies and related problems.

SUMMARY OF THE INVENTION

A system improves medical data acquisition with optimized data sampling and acquisition rate and automatic analog to digital parameter configuration and tuning using nonlinear and non-uniform data sampling, conversion and acquisition to capture and characterize real time dynamic medical signals, such as electrophysiological and hemodynamic signals. A patient monitoring signal processing system adaptively varies medical signal data rate. The system uses an analog to digital converter for digitizing an analog cyclically varying input signal derived from a patient in response to a sampling clock input. The sampling clock determines frequency of analog to digital sampling of the analog input signal by the analog to digital converter. A detector detects first and second different signal portions within a cycle of the cyclically varying input signal. A control processor coupled to the analog to digital converter and the detector, provides the sampling clock and adaptively determines first and second different frequencies of the sampling clock to be used in sampling within detected corresponding first and second different signal portions of the cyclically varying input signal in response to predetermined information indicating a frequency of a signal component of the cyclically varying input signal in the first signal portion is higher than a frequency of a signal component of the cyclically varying input signal in the second signal portion. Also the first frequency is higher than the second frequency of the first and second different frequencies.

DETAILED DESCRIPTION OF THE INVENTION

A system improves medical data acquisition with optimized data sampling and acquisition rates and automatic analog to digital parameter configuration and tuning using nonlinear and non-uniform data sampling of medical signals. The system adaptively accommodates variation in signals (e.g., surface ECG signals, intra-cardiac electrograms), in which a portion of the signal, such as a QRS complex portion (typically about 15-30% of whole heart cycle) is of higher frequency (and information) content than rest of the signal. Further, an automatic analog to digital parameter configuration and tuning function provides reliable and stable quantification and characterization of patient signals with high resolution and speed and reduces instrumentation conversion time and increases the life span of hardware and processing electronics. Known waveform and corresponding medical parameter analysis of cardiac depolarization and repolarization procedures focus on the QRS complex and depolarization of ECG signals (Electrophysiological signals) which may need a relatively high sampling rate (such as 400-1000 Hz).

In known systems a high speed analog to digital converter is used to digitize medical parameter signals and generates large amounts of data per second which may overload transmission and filtering modules and includes a substantial proportion of redundant signal information. This is especially so for medical signals (like ECG signals) in which a high frequency signal portion is a small proportion of the heart cycle. A system advantageously uses nonlinear and non-uniform signal and data sampling to adaptively tune and control an analog to digital (A/D) converter in response to the input signal itself, which enhances effectiveness and efficiency of data sampling and acquisition of medical signal data.

Figure 1:
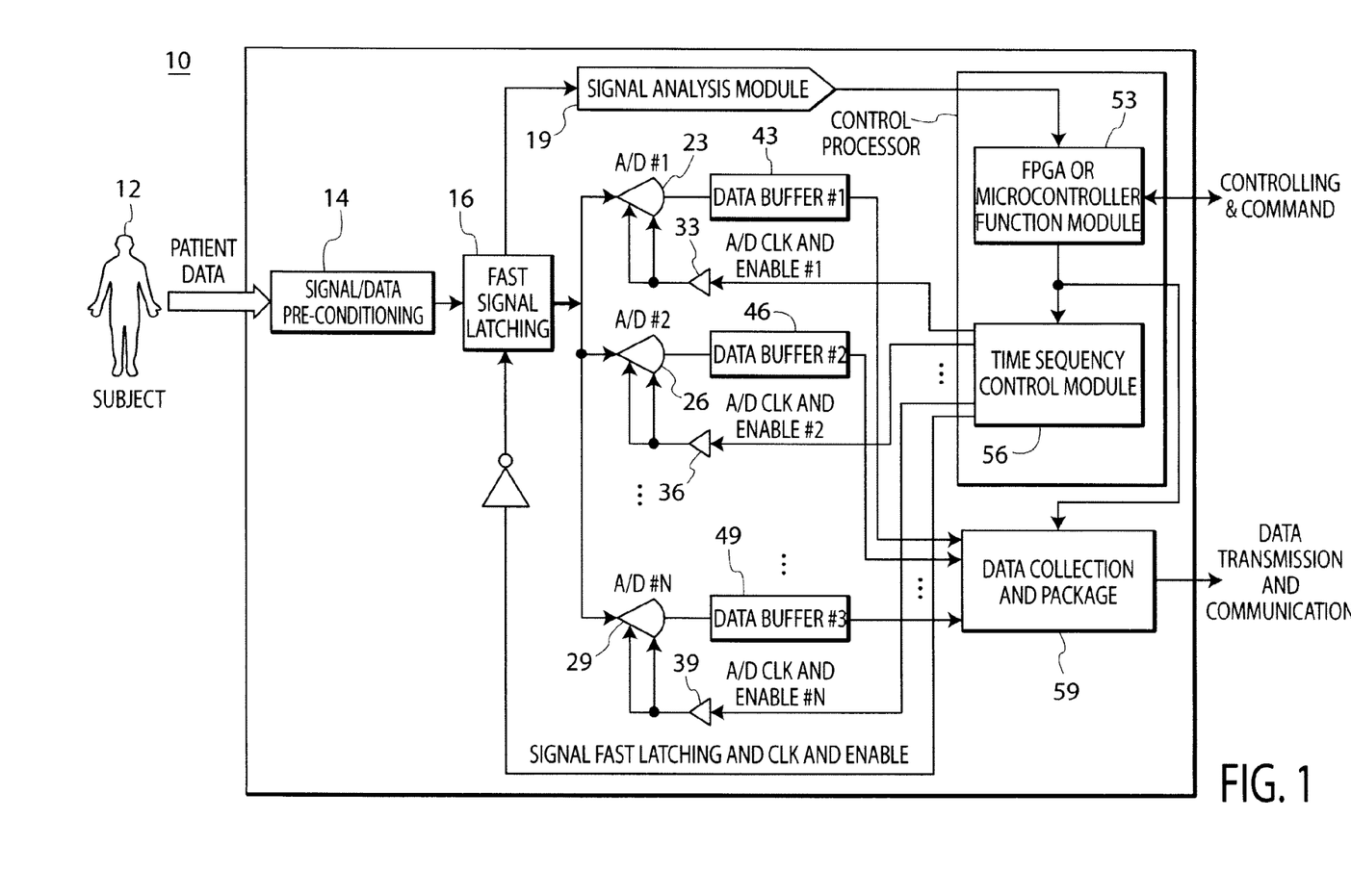
FIG. 1 shows a patient monitoring signal processing system for adaptively varying medical signal data rate, according to invention principles.

FIG. 1 shows patient monitoring signal processing system 10 for adaptively varying medical signal data rate in processing patient monitoring signals received from patient 12. System 10 improves the performance of clinical applications, especially of cardiac signal acquisition, analysis and interpretation. System 10 provides nonlinear and non-uniform medical signal sampling and data acquisition of signals (such as surface ECG and intra-cardiac electrograms (ICEG) signals) having unevenly distributed frequency components along a timeline. System 10 automatically adaptively adjusts sampling characteristics, based on medical signal real time characteristics and change in the characteristics. For example, in a fast signal portion (like a QRS complex portion), system 10 provides a relatively high sampling rate and provides a reduced sample rate during a relatively slow signal portion (such as a signal portion from a T wave to a P wave). System 10 in one embodiment uses a low sampling rate A/D converter to achieve high frequency signals by using fast signal latching implemented in hardware and software with automatic detection and analysis. The system increases sensitivity and stability of medical signal acquisition and employs virtual sampling to translate nonlinear and non-uniform sampled data (high frequency and low frequency sampled data within different portions of a signal), into uniform high speed sampling data via virtual data interpolation. The interpolation uses different kinds of linear interpolation function such as FFT (Fast Fourier transform), HHT (Hilbert—Huang transform), wavelet analysis or entropy calculation, for example.

System 10 automatically adaptively tunes and adjusts data sampling and conversion in response to input medical signal characteristics, such as dynamic frequency range and instantaneous frequency, for example. Electrophysiological signals (such as surface ECG signal, intracardiac electrograms), hemodynamic signals (such as pressure, blood flow parameters) and vital sign signals derived from patient 12 are preconditioned (amplified, filtered and buffered) by unit 14 and latched by fast latching function 16. Fast latching function 16 generates stable analog signals for A/D conversion by a set of N Analog to Digital converters 23, 26 . . . 29, which are electrically and functionally similar. Analog to Digital converters 23, 26 . . . 29 digitize analog cyclically varying input signals derived from patient 12 in response to a sampling clock input. The sampling clock determines frequency of analog to digital sampling of the received analog input signal by converters 23, 26 . . . 29 and is provided by timing and sequencing control module 56 via buffers 33, 36 . . . 39. Control module 56 also provides a control signal for switching fast latch module 16 via a buffered input. Digitized output data provided by converters 23, 26 . . . 29 is cached by data buffers 43, 46 . . . 49 respectively and provided to data aggregation unit 59 for communication to a destination device. Unit 59 aggregates, packetizes, sequences and time stamps digitized data for output. Unit 59 also in one embodiment interpolates the output data to provide intermediate data values in providing virtual re-sampled data and appends time stamps to the output data indicating time within a heart cycle and absolute time of acquisition of the data received from the patient.

A detector in signal analysis unit 19 detects first and second different signal portions within a cycle of the cyclically varying input signal derived from patient 12 and preprocessed and latched by unit 14 and 16, respectively. A control processor (comprising units 53 and 56) coupled to analog to digital converters 23, 26 . . . 29 and the detector, provides the sampling clock and adaptively determines first and second different frequencies of the sampling clock to be used in sampling within detected corresponding first and second different signal portions of the cyclically varying input signal. The control processor provides the sampling clock in response to predetermined information indicating a frequency of a signal component of the cyclically varying input signal in the first signal portion is higher than a frequency of a signal component of the cyclically varying input signal in the second signal portion. Also, the first frequency of the first and second different frequencies is higher than the second frequency. The control processor tunes and adjusts working time sequence and speed (i.e., clock sampling rate) of A/D converters 23, 26 . . . 29.

Different kinds of input signals and different portions of an individual signal may substantially vary along a timeline. For example, in surface ECG signals, the high frequency signal components are in a heart beat (periodic signal) QRS complex portion (the depolarization portion) having a highest frequency component typically up to 250 Hz. For other parts of one hear beat, such as a P wave or T wave, for example, the highest frequency component is usually less than 50 Hz. The known typical signal parameter ranges and limits are stored in data in the control processor and enable selection of a substantially optimum dynamically varying sampling rate for data acquisition and A/D conversion.

System 10 analyzes an input signal derived from patient 12 by deriving knowledge of signal frequency bands (such as a highest instant frequency component). System 10 analyzes the input signal itself to derive data for feedback and control. The control processor uses stored known medical signal parameters identifying characteristics of patient physiological (e.g., ECG) signals to simplify signal analysis and component characterization procedures. For example, an ECG signal is periodic and heart beat cycle length is determined (e.g., using RR wave detection), for use in accurately identifying fast signal components and slow signal components in the real time signals. Function control module 53 (such as an FPGA (Field Programmable Gate Array) or a microcontroller) and unit 56 in the control processor adaptively adjusts time clocks and sampling rate used for sampling and A/D conversion by units 23, 26 . . . 29 of incoming medical signals. The control processor determines how many A/D converter devices are activated and how these devices work together and data aggregation unit 59 aggregates, sequences and buffers multi-channel data (non-uniformed data) for communication to a destination device.

In one embodiment A/D converters 23, 26 . . . 29 are of medium cost and performance for processing a relatively fast signal component input of 400 Hz, for example. Signal analysis and recognition unit 19 also characterizes and conveys derived information and calculation results to function control unit 53. which in conjunction with timing control unit 56, adaptively tunes and adjusts how many A/D devices are used for signal sampling and data acquisition and determines data conversion and sampling rate and signal latching. For example, for a 400 Hz (highest frequency), a set of 6 A/D converters and a 2-4 kHz sampling clock are used. Typically, the higher the frequency of the input medical signal, the more A/D converters are used. Further, if a relatively slow signal component is input (such as a T wave in a surface ECG signal having 10-20 Hz components or less), one A/D converter with a typical 100 Hz data sampling clock rate is sufficient to capture details of the T wave signal portion. In one embodiment, system 10 includes an additional unit (in unit 53) for switching from data translation and conversion using non-uniform, nonlinear sampling to linear, uniform sampling. In another embodiment, a fast A/D converter and sampling unit is comprised of multiple slow A/D converters employing nonlinear and non-uniform sampling. This reduces cost and improves the efficiency. In one embodiment, system 10 is incorporated in a patient monitoring, pacemaker or other medical device, for example.

Figure 2:
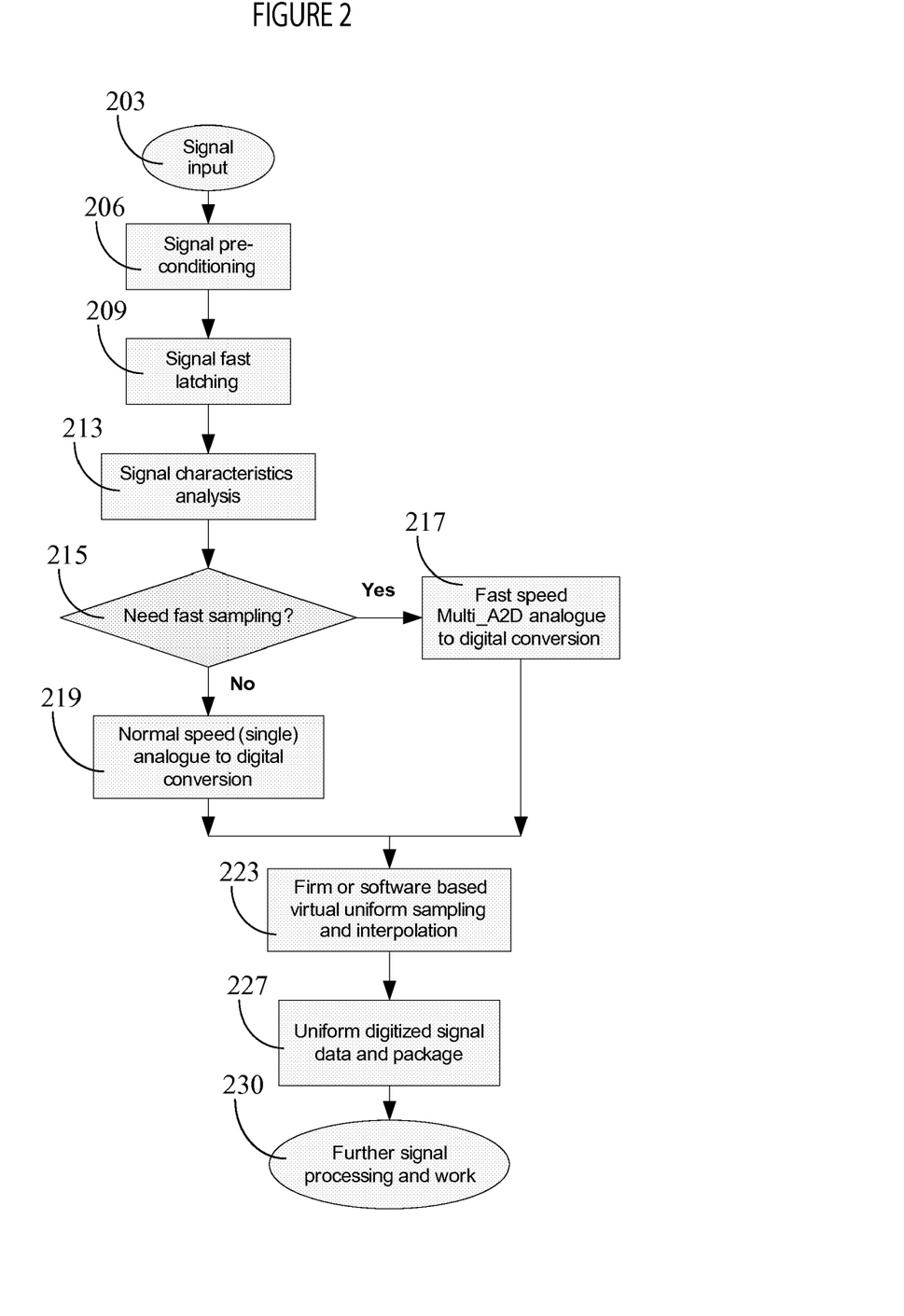
FIG. 2 shows a flowchart of a process used by a patient monitoring signal processing system for adaptively varying medical signal data rate in analog to digital conversion, according to invention principles

FIG. 2 shows a flowchart of a process used by patient monitoring signal processing system 10 (FIG. 1) for adaptively varying medical signal data rate in analog to digital conversion. In step 213 medical signals (such as ECG, ICEG signals received in step 203) are analyzed for characteristics by signal analysis unit 19 after signal pre-conditioning including filtering in step 206 by unit 14 and latching by unit 16 in step 209. A control processor (comprising units 53 and 56) in step 215 adaptively determines different frequencies of a sampling clock to be used in sampling within detected particular different signal portions of the cyclically varying input signal in response to signal analysis and recognition by unit 19. Specifically, the control processor selects a relatively fast sampling clock rate and a first number of A/D converters to use in step 217 in response to determining to use relatively fast sampling in step 215. The control processor determines to use relatively fast sampling in response to a determination a frequency of a signal component in a first signal portion is higher than a frequency of a signal component in a second signal portion. The control processor selects a relatively slow sampling clock rate and a second number (lower or equal to the first number) of A/D converters to use in step 219 in response to determining to use relatively slow sampling in step 215. The control processor determines to use relatively slow sampling in response to a determination a frequency of a signal component in a second signal portion is lower than a frequency of a signal component in the first signal portion.

Following sampling rate and A/D converter selection, A/D converters 23, 26 . . . 29 digitize a received input signal in step 223 using the selected A/D converters and sampling clock provided by unit 56. System 10 provides non-uniform and nonlinear virtual re-sampling and interpolation. Thereby: when a medical signal of relatively low frequency components is input, the control processor tunes the sampling rate to capture desired detail and the selected sampling rate does not add any additional noise and information to the acquired signals. In step 230, digitized output data provided by converters 23, 26 . . . 29 is cached by data buffers 43, 46 . . . 49 respectively and provided to data aggregation unit 59 for communication to a destination device for further processing.

Figure 3:
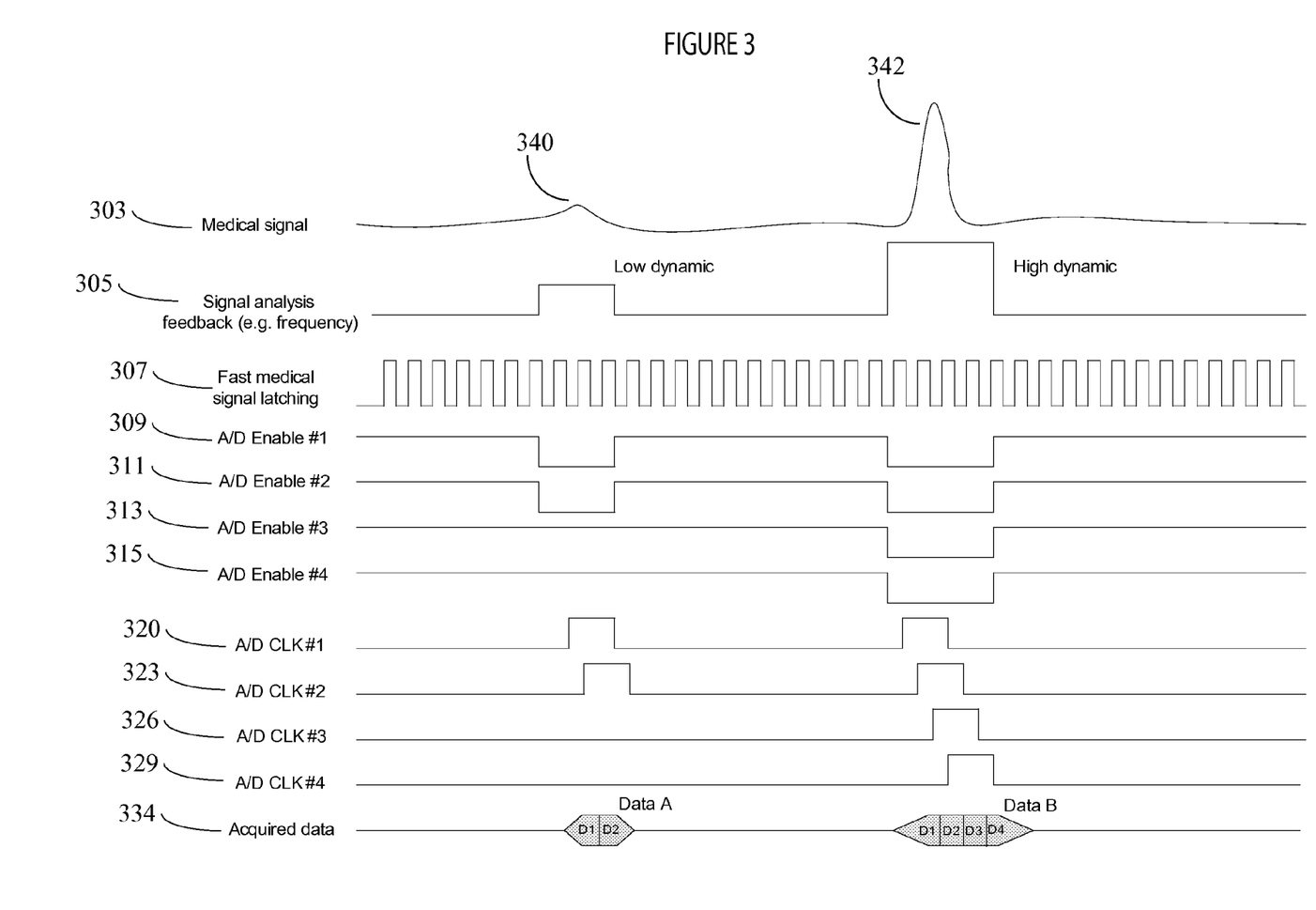
FIG. 3 illustrates adaptive analog to digital conversion control using nonlinear and non-uniform signal sampling and acquisition, according to invention principles.

FIG. 3 illustrates adaptive analog to digital conversion control using nonlinear and non-uniform real time input medical signal sampling and acquisition. Input patient medical signal 303 includes relatively fast frequency component signal portion 342 and relatively slow frequency component signal portion 340. The control processor captures and analyzes instantaneous signal characteristics to tune and adjust A/D converter (e.g. converter 23, 26 . . . 29 FIG. 1) sampling rate clocks 320, 323, 326 and 329. The control processor also provides signal feedback analysis signal 305 indicating high and low frequency portions and characteristics of input signal 303 and fast latching signal 307 for control of fast latch unit 16 (FIG. 1). The control processor also determines the number of A/D converters to use and their operational sequence for medical signal sampling and acquisition. The control processor analyzes the input signal characteristics and identifies two signal portions 340 and 342 having slow and fast signal components respectively, to be sampled and digitized and provides corresponding signal 305. In response to signal 305, the control processor determines that slow frequency component portion 340 of the input signal may be captured by two A/D converters and the high frequency component portion may be captured by four A/D converters. Further, in response to signal 305, the control processor in conjunction with timing and sequencing control module 56 generates A/D converter sampling rate clocks 320, 323, 326 and 329 and corresponding A/D converter enable signals 309, 311, 313 and 315. The A/D converters generate output digital data signal 334.

Figure 4:
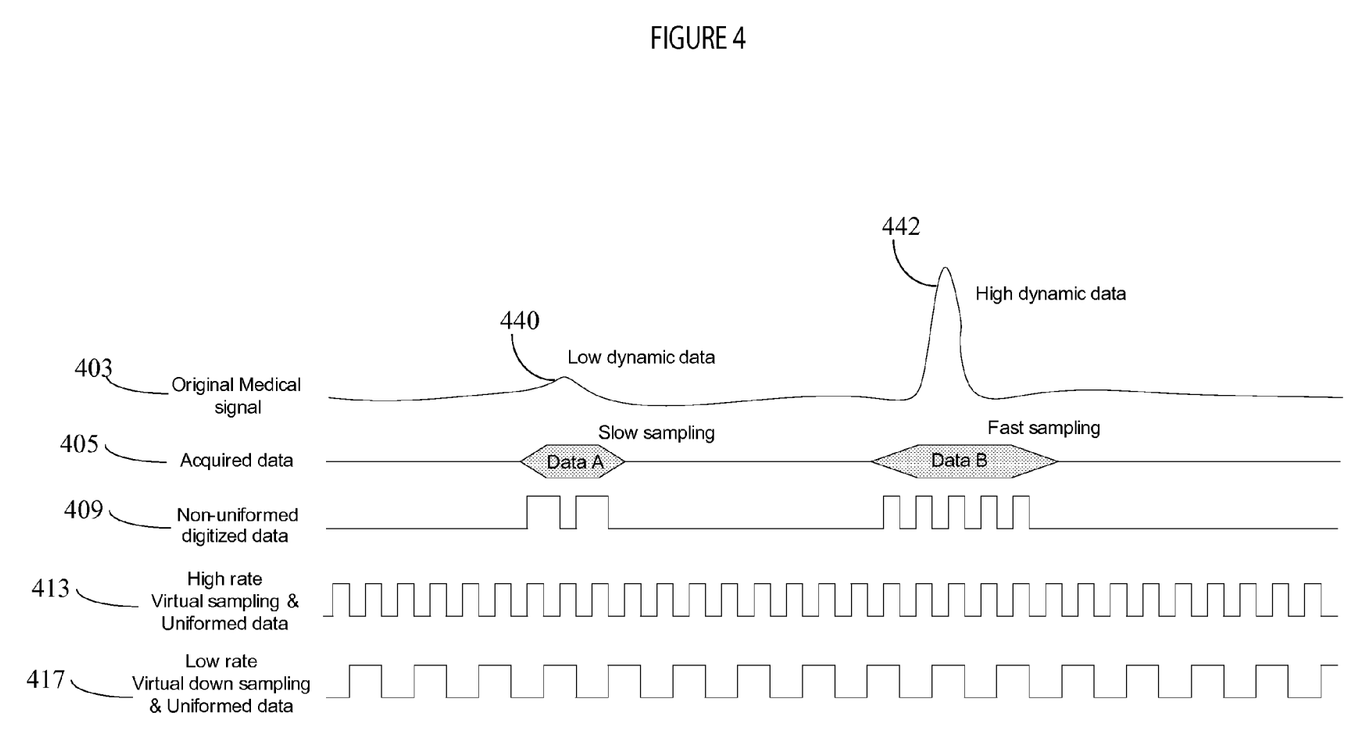
FIG. 4 illustrates adaptive analog to digital conversion control using virtual sampling and re-sampling rate selection and interpolation, according to invention principles.

FIG. 4 illustrates adaptive analog to digital conversion control using virtual sampling and re-sampling rate selection and interpolation. Unit 59 (FIG. 1) appends time stamps to slow and fast sampled data and data indicating a sampling frequency used for different portion of a signal. System 10 also in one embodiment employs uniform data interpolation and virtual re-sampling at the maximum frequency required for the data in response to data indicating a signal processing application or type of analysis to be performed. The data is sampled without additional information (such as noise) being added. Input signal data 403 having a low frequency component portion 440 and a relatively high frequency component portion 442 is sampled with clock signal 409 using A/D converters as described in connection with FIG. 3 to provide digitized data signal 405. The control processor (comprising units 53 and 56) of FIG. 1 adaptively resamples the digitized output data signal 409 data with a sampling rate selected in response to data indicating a signal processing application or type of analysis to be performed. In one application for example, a high frequency clock signal 413 is used and in another application a relatively low frequency clock signal 417 (for downsampling) is used. The selected re-sampling rate is less than or equal to the maximum sampling rate used in providing signal 405. Higher frequency re-sampling does not add any distortion in re-sampling the lower frequency portion of signal 405. System 10 adaptively selects a re-sampling rate and interpolation function. System 10 uses single order or multi-order interpolation for data matching in a gap between two data sampled regions of signal 405, for example.

System 10 may advantageously use low performance A/D converter devices such as generic A/D converters and may be implemented within an integrated controllable and programmable A/D device, for example. System 10 is usable for processing different kinds of medical signal, such as temperature, energy and pressure signals using stored predetermined information identifying medical signal parameters and characteristics facilitating adaptive generation of nonlinear and non-uniform sampling clocks. The system 10 nonlinear and non-uniform signal processing, data sampling and acquisition is controlled and adapted in response to input patient monitoring signals to provide optimized sensitivity, performance and efficiency. System embodiments employ different fixed sampling rates, different variable sampling rates and variable clock rate in nonlinear and non-uniform signal sampling. For example, a predetermined sampling rate based on a highest input signal instantaneous frequency component, such as 20 Hz sampling for a signal having components 1-10 Hz and 40 Hz for a signal having components 10-20 Hz. Fixed sampling rates in one embodiment are predetermined based on data indicating type of processing or clinical application.

The variable sampling rate embodiment is sensitive to the input signal and controls the signal sampling rate in real time. The embodiment provides accurate sampling clock control and sampling rate adjustment. For example, if a current instantaneous input signal frequency component is 67 Hz, system 10 signal feedback controls the clock and sampling rate to best match the sampling rate, e.g. to provide a 135 Hz optimized sampling rate. Further, if a typical input signal range is 10-30 Hz and suddenly a signal frequency component increases to 130 Hz, the system 10 control processor automatically adjusts a sampling clock frequency and sampling rate to accommodate the increased signal frequency in response to predetermined signal content and structure information (e.g. a look-up table associating signal frequency with sampling rate and indicating sampling rate or even no-sampling for predetermined portions of an input cyclic signal). This may be done in response to a signal component frequency exceeding a predetermined threshold such as 60 Hz, for example. If a signal frequency component is below a threshold frequency, a slow sampling rate table is used (10 Hz-20 Hz). If the signal is above the threshold, a sampling rate determined from a faster sampling rate table (e.g., 100 Hz-150 Hz) is used. The sampling rate table is used in one embodiment to implement the nonlinear and non-uniform sampling. Another embodiment uses adaptive best matching sampling frequency control which automatically uses a 2-3 times multiple, for example, of the frequency of the instantaneous highest signal frequency component of the input signal as the sampling rate. A further embodiment, gates sampling with a gating signal so that portions of an input signal are not sampled and instead during the gated portions default or null data is substituted, for example. In one embodiment, an automatically selected sampling frequency is derived by adaptively varying an A/D converter clock. System 10 provides nonlinear A/D converter operation together with circuit (or software) based virtual signal interpolation and uses relatively slow A/D converters to perform nonlinear and non-uniform sampling, to capture high frequency (fast) input signals.

Figure 5:
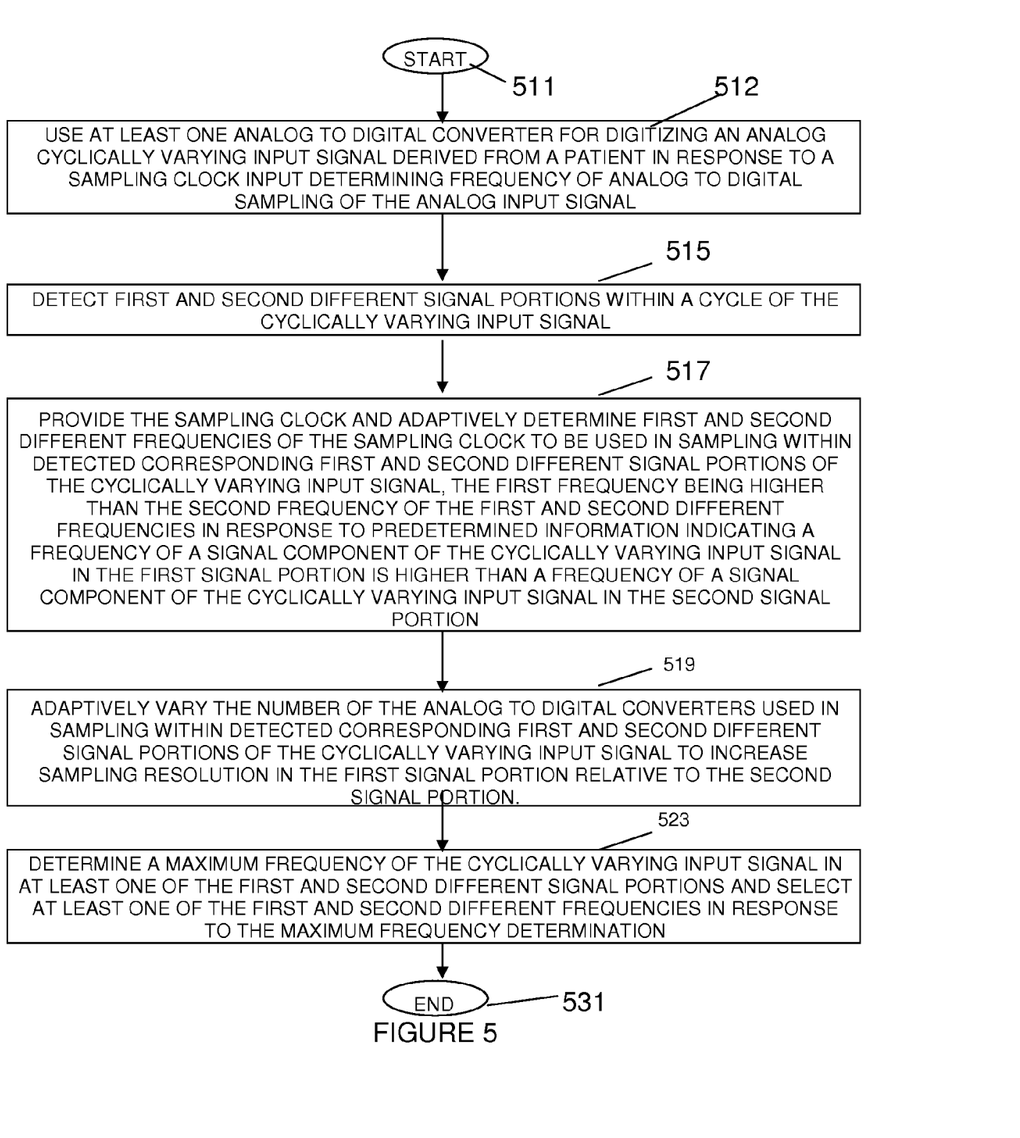
FIG. 5 shows a flowchart of a process used by a patient monitoring signal processing system for adaptively varying medical signal data rate, according to invention principles.

FIG. 5 shows a flowchart of a process used by patient monitoring signal processing system 10 (FIG. 1) for adaptively varying medical signal data rate. In step 512 following the start at step 511, A/D converters 23, 26 . . . 29 digitize an analog cyclically varying input signal derived from a patient in response to a sampling clock input. The sampling clock determines frequency of analog to digital sampling of the analog input signal by A/D converters 23, 26 . . . 29. Signal analysis unit (detector) 19 in step 515 detects first and second different signal portions within a cycle of the cyclically varying input signal. A control processor (units 53 and 56) is coupled to analog to digital converters 23, 26 . . . 29 and detector 19.

In step 517 the control processor provides the sampling clock and adaptively determines first and second different frequencies of the sampling clock to be used in sampling within detected corresponding first and second different signal portions of the cyclically varying input signal, in response to a control signal comprising predetermined information (or a measurement determination) indicating a frequency of a signal component of the cyclically varying input signal in the first signal portion is higher than a frequency of a signal component of the cyclically varying input signal in the second signal portion. The predetermined information indicates the first frequency is higher than the second frequency of the first and second different frequencies and may also indicate a predetermined structure of the cyclically varying input signal or the first signal portion is of more interest than the second signal portion. At least one of the first and second different frequencies is fixed or is variable in response to a determined frequency content of. the cyclically varying input signal. The control processor generates the control signal by determining whether a frequency of a signal component of the cyclically varying input signal in the first signal portion is higher than a frequency of a signal component of the cyclically varying input signal in the second signal portion.

The control processor adaptively determines the first and second different frequencies of the sampling clock in response to a determination a frequency of a signal component of the cyclically varying input signal in the first or second signal portions exceeds a predetermined frequency threshold or lies in a frequency range indicated using a look-up table. In one embodiment, the control processor adaptively selects at least one of the first and second different frequencies to be zero and inhibits sampling during a corresponding first and second different signal portion. In another embodiment, the detector detects a third signal portion within the cycle of the cyclically varying input signal. Further, the control processor adaptively selects a frequency of the sampling clock to be zero in the third signal portion and inhibits sampling during the third signal portion.

In step 519, the control processor adaptively varies the number of the analog to digital converters used in sampling within detected corresponding first and second different signal portions of the cyclically varying input signal to increase sampling resolution in the first signal portion relative to the second signal portion. In one embodiment, in step 523 a calculation processor in unit 53 of the control processor, determines a maximum frequency of the cyclically varying input signal in at least one of the first and second different signal portions and selects at least one of the first and second different frequencies in response to the maximum frequency determination. The calculation processor selects at least one of the first and second different frequencies to be at least a two times multiple of a determined maximum frequency. The process of FIG. 5 terminates at step 531.

A processor as used herein is a device for executing machine-readable instructions stored on a computer readable medium, for performing tasks and may comprise any one or combination of, hardware and firmware. A processor may also comprise memory storing machine-readable instructions executable for performing tasks. A processor acts upon information by manipulating, analyzing, modifying, converting or transmitting information for use by an executable procedure or an information device, and/or by routing the information to an output device. A processor may use or comprise the capabilities of a controller or microprocessor, for example, and is conditioned using executable instructions to perform special purpose functions not performed by a general purpose computer. A processor may be coupled (electrically and/or as comprising executable components) with any other processor enabling interaction and/or communication there-between. A display processor or generator is a known element comprising electronic circuitry or software or a combination of both for generating display images or portions thereof.

An executable application, as used herein, comprises code or machine readable instructions for conditioning the processor to implement predetermined functions, such as those of an operating system, a context data acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters. A user interface (UI), as used herein, comprises one or more display images, generated by a display processor and enabling user interaction with a processor or other device and associated data acquisition and processing functions.

The UI also includes an executable procedure or executable application. The executable procedure or executable application conditions the display processor to generate signals representing the UI display images. These signals are supplied to a display device which displays the image for viewing by the user. The executable procedure or executable application further receives signals from user input devices, such as a keyboard, mouse, light pen, touch screen or any other means allowing a user to provide data to a processor. The processor, under control of an executable procedure or executable application, manipulates the UI display images in response to signals received from the input devices. In this way, the user interacts with the display image using the input devices, enabling user interaction with the processor or other device. The functions and process steps herein may be performed automatically or wholly or partially in response to user command. An activity (including a step) performed automatically is performed in response to executable instruction or device operation without user direct initiation of the activity. The system and processes of FIGS. 1-5 are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. System 10 is of particular use in processing patient medical signals, such as ECG, ICEG signals having a substantial portion containing relatively slow frequency signal components and a small part containing relatively high frequency signal components requiring relatively high rate sampling, for example. Further, the processes and applications may, in alternative embodiments, be located on one or more (e.g., distributed) processing devices on the network of FIG. 1. Any of the functions and steps provided in FIGS. 1-5 may be implemented in hardware, software or a combination of both.

What is claimed is:

1. A patient monitoring signal processing system for adaptively varying medical signal data rate, comprising:
   an analog to digital converter for digitizing an analog cyclically varying input signal derived from a patient in response to a sampling clock input, said sampling clock determining frequency of analog to digital sampling of said analog input signal by said analog to digital converter;
   a detector for detecting first and second different signal portions within a cycle of said cyclically varying input signal; and
   a control processor coupled to said analog to digital converter and said detector, for providing said sampling clock and adaptively determining first and second different frequencies of said sampling clock to be used in sampling within detected corresponding first and second different signal portions of said cyclically varying input signal, the first frequency being higher than said second frequency of said first and second different frequencies in response to predetermined information indicating a frequency of a signal component of said cyclically varying input signal in the first signal portion is higher than a frequency of a signal component of said cyclically varying input signal in the second signal portion.

2. A system according to claim 1, wherein
said control processor adaptively determines said first and second different frequencies of said sampling clock in response to a determination a frequency of a signal component of said cyclically varying input signal in the first signal portion is higher than a frequency of a signal component of said cyclically varying input signal in the second signal portion.

3. A system according to claim 1, wherein
said first and second frequencies are fixed.

4. A system according to claim 1, wherein
at least one of said first and second different frequencies is variable.

5. A system according to claim 3, wherein
at least one of said first and second different frequencies is variable in response to a determined frequency content of said cyclically varying input signal.

6. A system according to claim 1, including
a calculation processor for determining a maximum frequency of said cyclically varying input signal in at least one of said first and second different signal portions and selecting at least one of said first and second different frequencies in response to the maximum frequency determination.

7. A system according to claim 6, wherein
said calculation processor selects at least one of said first and second different frequencies to be at least a two times multiple of a determined maximum frequency.

8. A system according to claim 1, wherein
said control processor adaptively selects at least one of said first and second different frequencies to be zero and inhibits sampling during a corresponding first and second different signal portion.

9. A system according to claim 1, wherein
said detector detects a third signal portion within said cycle of said cyclically varying input signal and
said control processor adaptively selects a frequency of said sampling clock to be zero in the third signal portion and inhibits sampling during the third signal portion.

10. A system according to claim 1, including
a plurality of analog to digital converters for digitizing said analog cyclically varying input signal and
said control processor adaptively varies the number of said analog to digital converters used in sampling within detected corresponding first and second different signal portions of said cyclically varying input signal to increase sampling resolution in said first signal portion relative to said second signal portion.

11. A system according to claim 1, wherein
said control processor adaptively determines said first and second different frequencies of said sampling clock in response to a determination a frequency of a signal component of said cyclically varying input signal in the first or second signal portions exceeds a predetermined frequency threshold.

12. A system according to claim 11, wherein
said control processor adaptively determines said first and second different frequencies of said sampling clock in response to a determination a frequency of a signal component of said cyclically varying input signal in the first or second signal portions lies in a frequency range indicated using a look-up table.

13. A patient monitoring signal processing system for adaptively varying medical signal data rate, comprising:
   an analog to digital converter for digitizing an analog cyclically varying input signal derived from a patient in response to a sampling clock input, said sampling clock determining frequency of analog to digital sampling of said analog input signal by said analog to digital converter;
   a detector for detecting first and second different signal portions within a cycle of said cyclically varying input signal; and
   a control processor coupled to said analog to digital converter and said detector, for providing said sampling clock and adaptively determining first and second different frequencies of said sampling clock to be used in sampling within detected corresponding first and second different signal portions of said cyclically varying input signal, the first frequency being higher than said second frequency of said first and second different frequencies in response to a control signal.

14. A system according to claim 13, wherein
said control signal comprises predetermined information indicating a predetermined structure of said cyclically varying input signal.

15. A system according to claim 13, wherein
said control signal comprises predetermined information indicating said first signal portion is of more interest than said second signal portion.

16. A patient monitoring signal processing system for adaptively varying medical signal data rate, comprising:
   an analog to digital converter for digitizing an analog cyclically varying input signal derived from a patient in response to a sampling clock input, said sampling clock determining frequency of analog to digital sampling of said analog input signal by said analog to digital converter;

a detector for detecting first and second different signal portions within a cycle of said cyclically varying input signal; and a control processor coupled to said analog to digital converter and said detector, for providing said sampling clock and adaptively determining first and second different frequencies of said sampling clock to be used in sampling within detected corresponding first and second different signal portions of said cyclically varying input signal, the first frequency being higher than said second frequency of said first and second different frequencies in response to a determination a frequency of a signal component of said cyclically varying input signal in the first signal portion is higher than a frequency of a signal component of said cyclically varying input signal in the second signal portion.

17. A patient monitoring signal processing system for adaptively varying medical signal data rate, comprising:

a plurality of analog to digital converters for digitizing an analog cyclically varying input signal derived from a patient in response to a sampling clock input, said sampling clock determining frequency of analog to digital sampling of said analog input signal by one or more of said plurality of analog to digital converters;

a detector for detecting first and second different signal portions within a cycle of said cyclically varying input signal; and a control processor coupled to said analog to digital converter and said detector, for adaptively determining the number of said analog to digital converters used in sampling within detected corresponding first and second different signal portions of said cyclically varying input signal to increase sampling resolution in said first signal portion relative to said second signal portion in response to a control signal.

18. A system according to claim 17, wherein
said control signal comprises predetermined information indicating a frequency of a signal component of said cyclically varying input signal in the first signal portion is higher than a frequency of a signal component of said cyclically varying input signal in the second signal portion.

19. A system according to claim 17, wherein
said control processor generates said control signal by determining whether a frequency of a signal component of said cyclically varying input signal in the first signal portion is higher than a frequency of a signal component of said cyclically varying input signal in the second signal portion.

* * * * *